United States Patent [19]
Kaiser et al.

[11] 3,969,397
[45] July 13, 1976

[54] PROCESS FOR THE PREPARATION OF L-DOPA

[75] Inventors: Ado Kaiser, Neu-Frenkendorf; Marcel Scheer, Basel; Werner Häusermann, Neuallschwil; Leo Marti, Riehen, all of Switzerland

[73] Assignee: Hoffmann-La Roche Inc., Nutley, N.J.

[22] Filed: Dec. 11, 1969

[21] Appl. No.: 884,333

[30] Foreign Application Priority Data
Dec. 27, 1968 Switzerland.................. 19270/68

[52] U.S. Cl............................ 260/501.11; 260/519; 260/570.5 CA; 424/309
[51] Int. Cl.² .......................................... C07C 63/50
[58] Field of Search....................... 260/519, 501.11

[56] References Cited
UNITED STATES PATENTS 3,347,928  10/1967  Taub et al.......................... 260/519
3,366,679  1/1968  Reinhold et al. .................. 260/519
3,505,385  4/1970  Reinhold et al. .................. 260/519

OTHER PUBLICATIONS

Fieser, L. F. et al., *Organic Chemistry*, 3rd Edtn., (1956), Pub. Reinhold Pub. Corp., New York, p. 274 relied on.
Greenstein, J. P. et al., *Chemistry of the Amino Acids*, 1961–vol. 3, Pub. J. Wiley & Sons, N.Y., pp. 2174 & 2175 relied on.

*Primary Examiner*—James O. Thomas, Jr.
*Assistant Examiner*—James H. Reamer
*Attorney, Agent, or Firm*—Samuel L. Welt; Bernard S. Leon; Richard A. Gaither

[57] ABSTRACT

The present invention is directed to preparing L-Dopa, an agent effective in the treatment of Parkinson's Disease, from D,L-N-benzoyl-3-(4-hydroxy-3-methoxyphenyl) alanine utilizing dehydroabietylamine as a resolving agent and intermediates in this process.

19 Claims, No Drawings

PROCESS FOR THE PREPARATION OF L-DOPA

BACKGROUND OF THE INVENTION

Dopa (chemically 3,4-dihydroxy phenyl alanine) has been known for many years to be an intermediate in the biological pathway from tyrosine to epinephrine. Quite recently, L-Dopa, the L-enantiomorph of the racemate Dopa, has been found to be a remarkably effective therapeutic agent in the treatment of Parkinson's Disease. Until this finding, sufferers of Parkinson's Disease relied only upon hit or miss symptomatic drug therapy or on surgical procedures in the hope of relief from the effects of their affliction. Unfortunately, neither symptomatic drug therapy nor surgical procedures generally resulted in more than a temporary retardation from the effects of this serious malady. The art has long recognized the pressing need for a medicament which would serve to control this chronic disease. The recent finding that L-Dopa is effective in the treatment of Parkinson's Disease has buoyed the hope of many. However, good quality L-Dopa is not available except in the most minor amounts because quality L-Dopa is difficult to prepare by prior art techniques. Because of the paucity of good quality L-Dopa, even those in the most pressing need have had difficulty obtaining it. It is evident that the supply of L-Dopa must be dramatically increased.

SUMMARY OF THE INVENTION

The object of the present invention is to provide ample amounts of good quality L-Dopa by a simple and economic process. This end has been achieved in the novel combination of process steps described hereinafter which involve a particularly efficacious resolving agent.

To obtain L-Dopa in accordance with this invention, a racemate of the formula:

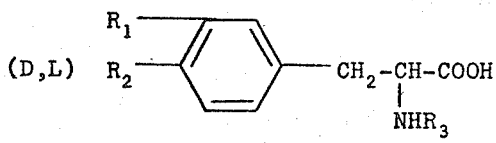

wherein $R_1$ is methoxy; $R_2$ is hydroxy, and $R_3$ is benzoyl;
is first treated with dehydroabietylamine which has the formula:

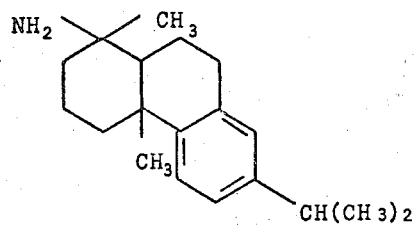

to yield a salt of the formula:

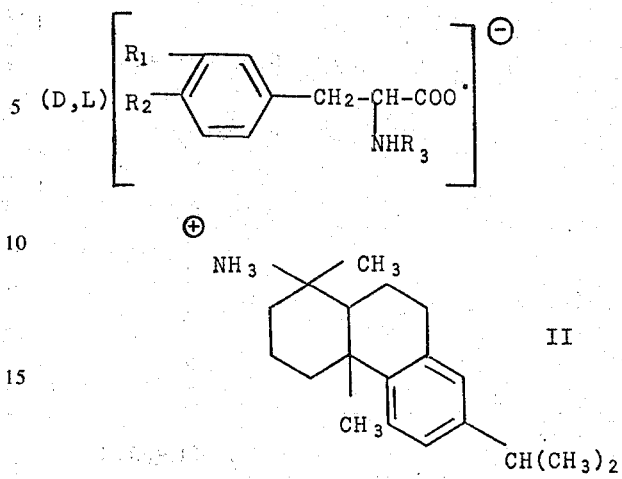

wherein $R_1$, $R_2$ and $R_3$ are as above.

The solubilities of the D and L forms of the salt are such that the L-salt of formula II can be made to precipitate from the solution in pure form leaving the D-salt of formula II in solution. The L-salt of formula II can be converted to L-Dopa by hydrolysis, whereas the D-salt of formula II can be racemized back to the D,L-acid of formula I.

Hence, by the above process, a simple and economic means is provided for producing L-Dopa in substantially pure form.

DETAILED DESCRIPTION OF THE INVENTION

As used herein the term "halogen" includes all four halogens, i.e., bromine, chlorine, iodine, and fluorine, with chlorine being preferred. The term "lower alkyl" comprehends both straight and branched chain saturated hydrocarbon moieties having from 1 to 6 carbon atoms such as methyl, ethyl, propyl, i-propyl, t-butyl and the like. Alkali metal has its usual meaning and includes such metals as lithium, sodium and potassium. The term lower alkanoic acid includes lower alkanoic acids containing from 1 to 6 carbon atoms such as acetic acid, formic acid, propionic acid, etc.

In accordance with this invention, the compound of formula I is produced by the following reaction scheme:

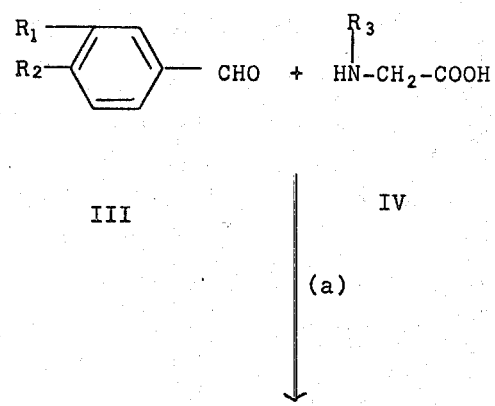

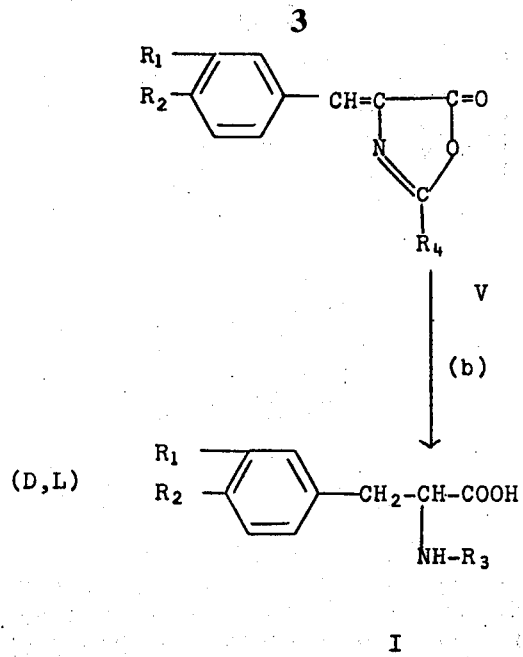

wherein $R_1$, $R_2$ and $R_3$ are as above; and $R_4$ is phenyl.

In step (a) a compound of the formula III is reacted with a compound of the formula IV to produce a compound of the formula V. This reaction is carried out in the presence of a lower alkanoic acid anhydride and a alkali metal salt of a lower alkanoic acid or alkali metal oxide. Any conventional lower alkanoic acid anhydride can be utilized in carrying out this reaction. AMong the lower alkanoic acid anhydrides, acetic anhydride is preferred. This reaction is also carried out in the presence of an anhydrous alkali metal salt of a lower alkanoic acid or an alkali metal oxide. The preferred alkali metal salt of a lower alkanoic acid which can be utilized in accordance with this invention is anhydrous sodium acetate. The preferred alkali metal oxide which can be utilized in this process is sodium oxide. The reaction of step (a) is preferentially effected in the presence of an inert organic solvent. Any conventional inert organic solvent can be utilized in carrying out this reaction. Among the preferred inert organic solvents are included dimethylformamide; ethers such as tetrahydrofuran, dimethylsulfoxide, etc.; and lower alkanols such as ethanol, methanol and the like. In carrying out this invention, temperature and pressure are not critical and this reaction can be carried out at room temperature and atmospheric pressure. However, it is generally preferred to conduct this reaction at the reflux temperature of the reaction medium.

The reaction of step (b) is carried out by subjecting the compound of formula V to catalytic hydrogenation. Any conventional means of catalytic hydrogenation can be utilized to convert the compound of the formula V to the compound of the formula I above. Generally, this hydrogenation is carried out in an aqueous alkaline medium. Any conventional inorganic alkali such as sodium hydroxide can be utilized to provide the alkaline medium. In carrying out this reaction, any conventional hydrogenation catalyst such as Raney-nickel, Raney-cobalt, platinum, palladium or the like can be utilized. This catalyst can be utilized with or without a carrier material such as charcoal or carbon. In carrying out this hydrogenation reaction, hydrogenation pressures of about 1 to about 50 atmospheres (gauge) are utilized. Generally, it is preferred to carry out this reaction at a hydrogenation pressure of from about 1 to about 20 atmospheres (gauge). In carrying out this reaction, temperature is not critical and this reaction can be carried out at room temperature. If desired, elevated temperatures such as 100°C. can be utilized. Generally, it is preferred to carry out this reaction at a temperature of from about 20° to about 60°C.

The compound of formula I above can be converted to L-Dopa, in accordance with this invention, by the following reaction scheme:

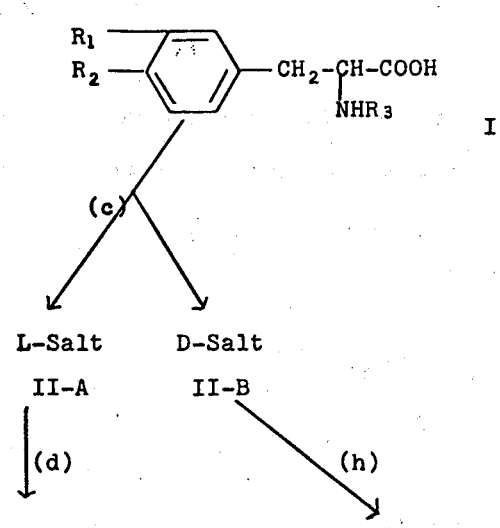

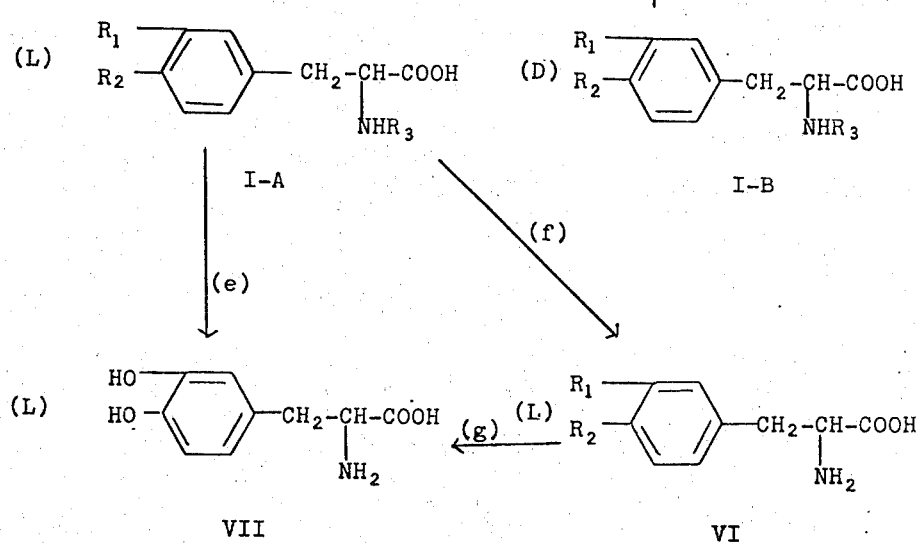

wherein $R_1$, $R_2$ and $R_3$ are as above.

The compound of formula I above is resolved, via reaction step (c), by reacting the compound of formula I with dehydroabietylamine. In this manner, the dehydroabietylamine salt of the L-acid (formula II-A) and the dehydroabietylamine salt of the D-acid (formula II-B) is formed. This reaction is carried out in an inert organic solvent preferably a lower alkanol solvent or in a mixture of water and a lower alkanol solvent. Any conventional lower alkanol can be utilized as the reaction medium. Among the preferred lower alkanol solvents are included methanol and ethanol. This reaction can be carried out by utilizing a temperature of from 20°C. to the reflux temperature of the reaction medium. Upon cooling to room temperature (35°C.) or below, (0°C.) the L-salt of formula II-A crystallizes out of solution with the D-salt of formula II-B remaining in solution. After cooling, the L-salt of formula II-A can be recovered in high yields from the mother liquors by filtration. In this treatment step, it is preferred that there be utilized for every one mole of the racemate of formula I above, from about 0.40 to about 1.6 moles of dehydroabietylamine; more preferably from about 0,4 to 1 mole.

The crystallization of the desired L-salt of formula II-A from the mother liquor can be aided through seeding. This seeding is carried out by contacting the reaction medium with a small amount of crystalline L-salt of formula II-A. This seeding is not essential, however, its use increases the ease of crystallization of the desired enantiomorph. In accordance with another embodiment of this invention, the compound of formula I is converted into the desired L-salt of formula II-A by first reacting one mole of the racemate of formula I above with from 0.4 to 0.6 moles, preferably 0.5 moles, of an alkali metal hydroxide, ammonia or an organic amine, and with 0.4 to 0.6 moles of dehydroabietylamine. In this reaction, the dehydroabietylamine is added to the reaction medium in an amount of from about 0.4 to about 0.6 moles, preferably 0.5 moles, per mole of the racemate of formula I. The reaction medium utilized in carrying out this embodiment of this invention can be any lower alkanol such as methanol or ethanol. If desired, the solvent can consist of the lower alkanol itself or can constitute a mixture of water and a lower alkanol.

In carrying out this embodiment of this invention, any alkali metal hydroxide, preferably sodium hydroxide or any primary, secondary, or tertiary amine, preferably diethyl amine, piperidine or triethyl amine can be utilized. This reaction can be carried out by heating to a temperature of from 40°C. to the reflux temperature of the solvent. Upon cooling to 0°C. to room temperature, the L-salt of formula II-A precipitates from the solution in crystalline form.

The operation of this embodiment of the process of this invention can be explained as follows:

When one mole of the racemate of the formula I is reacted with 0.4 to 0.6 moles of an alkali metal hydroxide, ammonia or an organic amine and from 0.4 to 0.6 moles of dehydroabietylamine, a mixture results. This mixture consists of one-half mole of the dehydroabietylamine salt of the L-antipode of the compound of formula I (compound II-A) and one-half mole of the alkali metal, ammonium or organic amine salt of the D-antipode of the compound of formula I. The L-salt of formula II-A precipitates out of the solvent medium while the alkali metal, ammonium or organic amine salt of the D-antipode of formula I above remains in solution. In this manner, the L-salt of formula II-A is easily obtained from the compound of formula I above.

The process step (c) is a particularly salient in that it provides a salt of formula I above which is easily separable in high purity from the reaction mixture in which it is formed. This capability of the salt of formula I above to be easily separated into its two optical antipodes without repeated and/or involved complicated crystallization procedures is surprising.

The resulting L-salt of the formula II-A above is converted to the compound of formula I-A, via reaction step (d) by neutralizing the compound of the formula II-A with an acid or base by conventional procedures. Any base capable of effecting the neutralizing step is suitable for the purposes of the present invention. However, a preferred base is an alkali metal hydroxide, e.g., sodium hydroxide, sodium carbonate, etc. A suitable neutralizing acid is a mineral acid such as hydrogen bromide, hydrogen chloride, etc.

The compound of formula I-A is converted to the compound of formula VII either directly via reaction step (e) or via an intermediate of the formula VI by reaction steps (f) and (g).

To obtain a compound of the formula VII (L-Dopa) directly from a compound of the formula I-A, the compound of the formula I-A is heated at reflux temperatures with a concentrated aqueous hydrohalic acid. The reaction of step (e) can take place with any conventional concentrated hydrohalic acid such as constant boiling hydrobromic acid or concentrated hydrochloric acid. Generally, it is preferred to carry out this reaction at a temperature of from about 120° to about 200°C. under pressure.

The two-step conversion of the compound of formula I-A into the compound of the formula VII (L-Dopa) is carried out by heating the compound of the formula I-A with a 2 to 4N-aqueous mineral acid such as hydrochloric acid or sulfuric acid. The reaction of step (f) deacylates the amino group on the compound of formula I-A. The reaction of step (f) is effected preferentially at elevated temperatures, e.g., at about reflux temperature. The compound of formula VI is converted to the compound of formula VII by the procedure set forth in connection with step (e).

After the separation of the L-salt of formula II-A from the reaction medium formed in reaction step (c), the dehydroabietylamine salt of the D-enantiomorph of the compound of formula I (compound II-B) or the alkali metal, ammonium or organic amine salt of the D-enantiomorph of the compound of formula I remains in solution. This salt can be separated from the mother liquors by conventional procedures, e.g., solvent removal or extraction. This D-enantiomorph salt is converted into the compound of formula I-B, via reaction (h) by utilizing the same procedures described in connection with reaction (d). The compound of formula I-B can be easily converted into the racemate of formula I by treating the compound of formula I-B with an anhydride of a carboxylic acid in the presence of a base. Any conventional anhydride of a carboxylic acid can be utilized in this process. Generally, it is preferred to utilize anhydrides of lower aliphatic carboxylic acids containing from 1 to 4 carbon atoms such as acetic anhydride, propionic acid anhydride or an anhydride of an aromatic carboxylic acid such as benzoic acid anhydride. Furthermore, in carrying out this invention, any conventional base can be utilized. Among the bases which can be utilized are inorganic bases such as alkali or alkaline earth metal hydroxides or organic bases such as a tetra lower alkyl ammonium hydroxide. Generally, the reaction of step (i) can be carried out utilizing the base as the reaction medium. However, this reaction can take place in an aqueous medium or in an organic solvent. In carrying out this racemization reaction, temperature and pressure are not critical and this reaction can be carried out at room temperature and atmospheric pressure. However, if desired, elevated temperatures and pressures can be utilized.

By means of the process of steps (h) and (i), the D-enantimorph recovered from the mother liquor formed after the separation of the L-salt of formula II-A is recovered and recycled. From a commercial point of view, this is important since it avoids the accumulation of unusable D-enantimorph.

It is understood that the following examples are representative and not limitative of the foregoing invention. All temperatures stated are in degrees centigrade. The petroleum ether utilized in these examples has a boiling point of 60° to 80°C. When ether is referred to in the examples, diethyl ether is meant.

EXAMPLE 1

31.5 g. of D,L-N-benzoyl-3-(4-hydroxy-3-methoxyphenyl)-alanine and 28.5 g. of dehydroabietylamine are placed in about 80 ml. of absolute methanol and heated. On boiling, all of the reactants dissolve. The resulting solution is then allowed to cool so that a precipitate is formed. After 22 hours at room temperature the precipitate is filtered off and rinsed portionwise with a total of 50 ml. of ice-cold methanol, then with diethyl ether, and dried at 60°C. under vacuum. For recrystallization, this salt is dissolved in 800–1,000 ml. of boiling methanol, filtered off hot, concentrated to about 100 ml. (whereby the substance begins to crystallize out), left to stand at room temperature for an hour, thereupon treated with 700 ml. of diethyl ether and left to stand overnight at 0°C. On the next morning, it is filtered, washed with ether and dried. 28.6 g. of dehydroabietylamine salt of the L-antipode are obtained in the form of white crystals with a melting point of 232°–233°C.; $[\alpha]_D^{24} = +55.0°$ ($c = 1$ in methanol). A second recyrstallization does not raise the rotation.

EXAMPLE 2

27 g. of the dehydroabietylamine salt of the L-antipode prepared in Example 1 are treated in a shaking funnel with 800 ml. of cold methanol and 200 ml. of 2-N caustic soda. The resulting clear solution is extracted with two portions each of 600 ml. of petroleum ether. The methanol is evaporated off from the aqueous-methanolic layer. The residue is made congoacidic with concentrated hydrochloric acid. To this acidified residue, ice is added and then the residue is extracted twice with 600 ml. of ethyl acetate each time. The ethyl acetate layers are washed twice with saturated aqueous sodium chloride solution, dried over anhydrous sodium sulfate and evaporated to an oil. This residue is sprinkled with isopropyl ether and allowed to stand at room temperature to form crystals. The residue is then treated with a little petroleum ether and allowed to stand overnight at 0°C. After filtering off and rinsing with petroleum ehter, for recrystallization this substance is dissolved in hot ethyl acetate, then left to cool to room temperature (whereupon recrystallization begins) and treated gradually with a little petroleum ether. After standing overnight at 0°C., the crystalline precipitate is filtered off and rinsed with petroleum ether. There are obtained 11.7 g. of pure L-N-benzoyl-3-(4-hydroxy-3-methoxyphenyl)-alanine with a melting point of 154°C. and a rotation of $[\alpha]_D^{24} = -32.7°$ ($c = 1$ in methanol). Further recrystallization does not alter the rotation value.

EXAMPLE 3

5 g. of L-N-benzoyl-3-(4-hydroxy-3-methoxyphenyl)-alanine are treated under a nitrogen atmosphere with 40 ml. of colorless aqueous solution containing 48% by weight hydrobromic acid and heated for 2½ hours in a 140°C. bath. The dark-colored residue is cautiously evaporated on the rotary evaporator. After evaporation there resulted a mass permeated with crystals. This mass is added to about 80 ml. of distilled water and extracted with 2 portions of diethyl ether. In this manner, the benzoic acid formed is thereby extracted. The aqueous layer is evaporated to an oil, so that as much hydrobromic acid as possible is removed. A little distilled water is thereupon added and the mixture is once more vigorously evaporated. This operation is repeated.

The resulting dark-colored oil is thereupon dissolved in 20 ml. of distilled water and 10 ml. of acetonitrile to form a dark clear solution. This solution is cooled to room temperature and then treated with 5 ml. of propylene oxide. After about 15 minutes, the pH is tested, and if necessary adjusted to a value of 5.5–6 with further propylene oxide. At this pH almost colorless crystals precipitate. 100 ml. of acetonitrile are gradually added and the mixture is left to stand overnight at 0°C. The crystals are filtered and washed first with distilled water/acetonitrile 1:5 by volume and then with acetonitrile and finally then with diethyl ether. The crystals are recrystallized by dissolving them in distilled water in a sulfonation flask under constant stirring while saturated with $SO_2$ gas. The contents of the flask are warmed during this procedure. After all of the crystals have been dissolved, the heat source is thereupon removed and an inert nitrogen gas stream is led through the solution whereupon the crystallization begins. The mixture is left at 0°C. and filtered off on the next morning. The crystals are then rinsed with distilled water/acetonitrile (1:1 by volume mixture) then with acetonitrile alone and finally with diethyl ether and dried. There are obtained 2.2 g. of L-3-(3,4-dihydroxyphenyl)-alanine with a melting point of 281°–282°C. $[\alpha]_D^{24} = -11.8°$ ($c = 1$ in 1-N HCl).

EXAMPLE 4

76 g. of vanillin, 89.5 g. of hippuric acid, 75 g. of anhydrous sodium acetate, 150 ml. of acetic anhydride and 25 ml. of dimethylformamide are added in the stated order into a flask provided with a condenser and calcium chloride tube. The mixture is thereupon stirred at a bath temperature of 100°C. for 15–30 minutes. The bath is removed, and 700–1000 ml. of distilled water are added dropwise within about 15 minutes in such a way that the mixture does not become difficult to stir. The mixture is cooled by leaving it at 0°C. for 3–5 hours. The resulting precipitate is then filtered off and washed with abundant (6–8 portions) of cold distilled water. After drying the crystals under vacuum, there are obtained 131–136 g. of 2-phenyl-4-(o-acetyl-vanilylidene)-2-oxazolin-5-one as yellow crystals which melt at 190°–192°C.

EXAMPLE 5

280 g. of 2-phenyl-4-(o-acetyl-vanillylidene)-2-oxazolin-5-one in 6 l. of distilled water are treated with 250 g. of solid pure sodium hydroxide and then with 70 g. of Raney-nickel and hydrogenated at 60°C. and 100 atmospheres (gauge). The hydrogenation mixture is thereupon filtered off, the catalyst rinsed with distilled water, the filtrate warmed to 60°C. in an open vessel and cautiously made congo-acidic (pH about 2) with concentrated hydrochloric acid. The product is allowed to crystallize out by standing overnight at 0°C. The crystals are then filtered off and washed with 3 portions of ice-cold distilled water and dried in vacuum at 60°C.

For purification, the crude crystalline material, while still hot, is dissolved in 400 ml. of methanol. After this, 800 ml. of distilled water are cautiously added and the mixture is seeded if necessary. The solution is allowed to stand overnight at 0°C. to form crystals. The crystals are filtered off, rinsed with distilled water and dried. 189 g. of D,L-N-benzoyl-3-(4-hydroxy-3-methoxyphenyl)-alanine are obtained as colorless crystals of melting point 160°–161°C.

EXAMPLE 6

31.5 g. of D,L-N-benzoyl-3-(4-hydroxy-3-methoxyphenyl)-alanine are dissolved in 50 ml. of methanol at 50°C. At the same time, likewise at 50°C., 14.2 g. of dehydroabietylamine (0.05 mole) are dissolved in 20 ml. of methanol. The methanolic dehydroabietylamine solution is poured into the acid solution and the flask rinsed with 5 ml. of methanol. After seeding, crystallization of the dehydroabietylamine salt of the L-antipode occurs. The mixture is allowed to stand overnight at room temperature and the crystals are filtered off on the following morning. After rinsing with 50 ml. of methanol at 0°C. and drying in vacuum at 60°–70°C., there are obtained 18.8 g. of dehydroabietylamine salt of the L-antipode with the specific rotation $[\alpha]_D^{20} = +49.9°$ ($c = 1$ in methanol).

EXAMPLE 7

27 g. of the dehydroabietylamine salt of the L-antipode prepared in Example 6 are treated in a shaking funnel with 800 ml. of cold methanol and 200 ml. of 2-N caustic soda. The resulting clear solution is extracted with two portions each of 600 ml. of petroleum ether. The methanol is evaporated off from the aqueous-methanolic layer. The residue is made congo-acidic with concentrated hydrochloric acid. To this acidified residue there is added ice and the residue is extracted twice with 600 ml. of ethyl acetate each time. The ethyl acetate layers are washed twice with saturated aqueous sodium chloride solution, dried over anhydrous sodium sulfate and evaporated to an oil. This residue is sprinkled with isopropyl ether, allowed to stand at room temperature to form crystals. The crystals are treated with a little petroleum ether and allowed to stand overnight at 0°C. The resulting crystalline precipitate is filtered and rinsed with petroleum ether. The recrystallization, this crystalline substance is dissolved in hot ethyl acetate then left to cool to room temperature (whereupon crystallization begins) and gradually treated with a little petroleum ether. After allowing the mixture to stand overnight at 0°C., the crystals are filtered off and rinsed with petroleum ether. There are obtained 11.7 g. of pure L-N-benzoyl-3-(4-hydroxy-3-methoxyphenyl)-alanine with a melting point of 154°C. and a rotation of $[\alpha]_D^{24} = -32.7°$ ($c = 1$ in methanol). Further recrystallization does not alter the rotation value.

EXAMPLE 8

14 g. of L-N-benzoyl-3-(4-hydroxy-3-methoxyphenyl)-alanine are heated at reflux in 150 ml. of 3-N aqueous hydrochloric acid for 15 hours. The cooled solution is then extracted twice with 100 ml. of diethyl ether, each time, and the ether extracts are evaporated under vacuum. The residue is dissolved in 10 ml. of water and 20 ml. of ethanol. This solution is treated with 10 ml. of propylene oxide and heated at reflux for a further 14 hours. The crystals which separate out on cooling are filtered off and recrystallized once from water. There are thus obtained 8 g. of L-3-(4-hydroxy-3-methoxyphenyl)-alanine with a melting point of 233°–236°C. $[\alpha]_D^{23} = -5.8°$ ($c = 1$ in 1-N HCl).

EXAMPLE 9

The conversion of L-3-(4-hydroxy-3-methoxyphenyl)-alanine into L-3-(3,4-dihydroxyphenyl)-alanine is effected by utilizing the procedure set forth in Example 3.

EXAMPLE 10

50 ml. of 1-N caustic soda (0.05 mole) and 80 ml. of methanol are added to 31.5 g. of D,L-N-benzoyl-3-(4-hydroxy-3-methoxyphenyl)-alanine (0.1 mole). On warming to 50°C., the alanine goes into solution. At the same time, likewise at about 50°C., 14.2 g. of dehydroabietylamine (0.05 mole) are dissolved in 30 ml. of methanol. The methanolic dehydroabietylamine solution is added to the alanine solution and the flask is rinsed with 10 ml. of methanol. The crystallization of the dehydroabietylamine salt of the L-antipode occurs very rapidly. This mixture is left to stand overnight at room temperature and the crystals filtered off on the following morning. After rinsing the crystals with 50 ml. of methanol/water (1:1 parts by volume) at a temperature of about 10°C. and drying, there are obtained 27 g. of dehydroabietylamine salt of the L-antipode with the specific rotation $[\alpha]_D^{20} = +49.5°$ ($c = 1$ in methanol).

EXAMPLE 11

The conversion of the dehydroabietylamine salt of the L-antipode to L-3-(3,4-dihydroxyphenyl)-amine is carried out by the procedures given in Examples 2 and 3.

EXAMPLE 12

50 ml. of 1-N ammonia (0.05 mole) and 80 ml. of methanol are added to 31.5 g. of D,L-N-benzoyl-3-(4-hydroxy-3-methoxyphenyl)-alanine (0.1 mole). On warming to 50°C., the alanine goes into solution. At the same time, likewise at 50°C., 14.2 g. of dehydroabietylamine (0.05 mole) are dissolved in 30 ml. of methanol. The methanolic dehydroabietylamine solution is added to the acid solution and the flask is rinsed with 10 ml. of methanol. The crystallization of the dehydroabietylamine salt of the L-antipode occurs very rapidly. This mixture is allowed to stand overnight at room temperature and the crystals are filtered on the following morning. After rinsing the crystals with 50 ml. of methanol/water (1:1 parts by volume) about 10°C. and drying, there are obtained 26.7 g. of dehydroabietylamine salt of the L-antipode with the specific rotation $[\alpha]_D^{20} = +49.8°$ ($c = 1$ in methanol).

EXAMPLE 13

The conversion of the dehydroabietylamine salt of the L-antipode to L-3-(3,4-dihydroxyphenyl)-alanine is carried out by the procedure given in Examples 2 and 3.

EXAMPLE 14

50 ml. of a 1-N aqueous diethylamine solution (0.05 mole) and 80 ml. of methanol are added to 31.5 g. of D,L-N-benzoyl-3-(4-hydroxy-3-methoxyphenyl)-alanine (0.1 mole). On warming to 50°C., the alanine goes into solution. At the same time, likewise at 50°C., 14.2 g. of dehydroabietylamine (0.05 mole) are dissolved in 30 ml. of methanol. The methanolic dehydroabietylamine solution is added to the alanine solution and the flask is rinsed with 10 ml. of methanol. The crystallization of the dehydroabietylamine salt of the L-antipode occurs very rapidly. The mixture is allowed to stand overnight at room temperature and the crystals filtered on the following morning. After rinsing with 50 ml. of methanol/water (1:1 by volume) at about 10°C. and drying, there are obtained 26.6 g. of dehydroabietylamine salt of the L-antipode with the specific rotation $[\alpha]_D^{20} = +49.8°$ ($c = 1$ in methanol).

EXAMPLE 15

The conversion of the dehydroabietylamine salt of the L-antipode to L-3-(3,4-dihydroxyphenyl)-alanine is carried out by the procedure given in Examples 2 and 3.

EXAMPLE 16

50 ml. of a 1-N aqueous piperidine solution (0.05 mole) and 80 ml. of methanol are added to 31.5 g. of D,L-N-benzoyl-3-(4-hydroxy-3-methoxyphenyl)-alanine (0.1 mole). On warming to 50°C., the alanine goes into solution. At the same time, likewise at 50°C., 14.2 g. of dehydroabietylamine (0.05 mole) are dissolved in 30 ml. of methanol. The methanolic dehydroabietylamine solution is added to the alanine solution and the flask is rinsed with 10 ml. of methanol. The crystallization of the dehydroabietylamine salt of the L-antipode occurs very rapidly. The mixture is allowed to stand overnight at room temperature and the crystals filtered off on the following morning. After rinsing the crystals with 50 ml. of methanol/water (1:1 parts by volume) at 10°C. and drying, there are obtained 26.4 g. of dehydroabietylamine salt of the L-antipode with the specific rotation $[\alpha]_D^{20} = +49.4°$ ($c = 1$ in methanol).

EXAMPLE 17

The conversion of the dehydroabietylamine salt of the L-antipode to L-3-(3,4-dihydroxyphenyl)-alanine is carried out by the procedure given in Examples 2 and 3.

EXAMPLE 18

27 g. of dehydroabietylamine salt of the D-antipode are treated in a separating funnel in the cold with 300 ml. of methanol and 100 ml. of 1-N caustic soda and extracted with 2 portions each of 200 ml. of petroleum ether. The aqueous methanolic layer is freed from methanol by evaporation on a rotary evaporator and the residue is adjusted to pH 1–2 with concentrated hydrochloric acid while cooling. The acidified residue is subsequently extracted twice with 500 ml. of ethyl acetate, each time, the organic layers are rinsed twice with aqueous saturated sodium chloride solution, dried over anhydrous sodium sulfate and evaporated to an oil. This oil is treated in a sulfonation flask with 40 ml. of 1-N caustic soda while stirring and then to this oil there is added 60 ml. of acetic acid anhydride dropwise while care is maintained so that the internal temperature of the flask does not exceed 50°C. This mixture is subsequently further stirred for 4 hours at 50°C. bath temperature, evaporated in vacuum to an oil and this partitioned between 200 ml. of distilled water and 300 ml. of ethyl acetate. The ethyl acetate layers are rinsed twice with saturated aqueous sodium chloride solution, dried over anhydrous sodium sulfate and evaporated to an oil. There are obtained 13 g. of D,L-N-benzoyl-3-(4-hydroxy-3-methoxyphenyl)-alanine with a rotation value of [α]$_D$ = about −1.7° (c = 1 in methanol).

We claim:

1. A compound of the formula

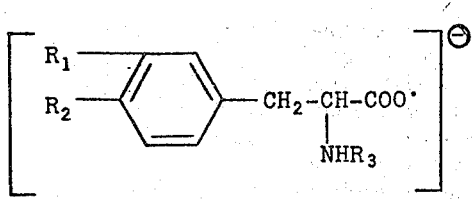

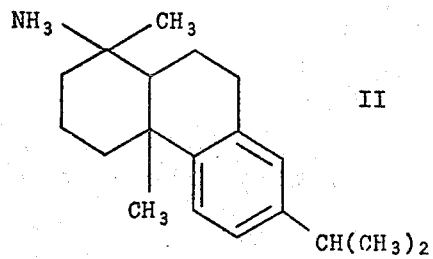

wherein $R_1$ is methoxy; $R_2$ is hydroxy and $R_3$ is benzoyl.

2. A compound as defined in claim 1 wherein said compound is the dehydroabietylamine salt of D-N-benzoyl-3-(4-hydroxy-3-methoxyphenyl)-alanine.

3. A compound as defined in claim 1 wherein said compound is the dehydroabietylamine salt of L-N-benzoyl-3-(4-hydroxy-3-methoxyphenyl)-alanine.

4. The compound of claim 1 wherein said compound is the dehydroabietylamine salt of D,L-N-benzoyl-3-(4-hydroxy-3-methoxyphenyl)-alanine.

5. The process for preparing the L-antipode of a salt of the formula:

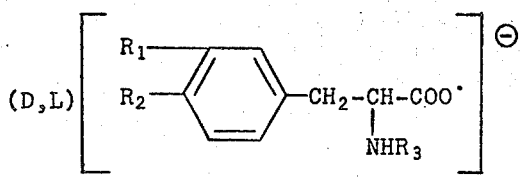

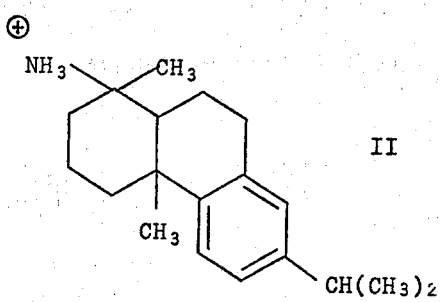

wherein $R_1$ is methoxy; $R_2$ is hydroxy and $R_3$ is benzoyl
comprising reacting a solution of the racemate of the formula:

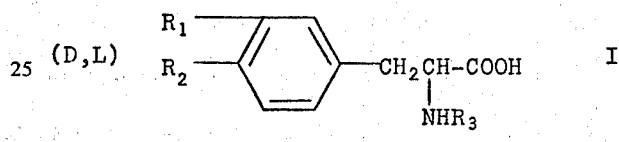

where $R_1$, $R_2$ and $R_3$ are as above
in an inert organic solvent with dehydroabietylamine to form said L-antipode as a crystalline precipitate with the D-antipode of said salt remaining in solution.

6. The process of claim 5 wherein said solvent is a lower alkanol.

7. The process of claim 5 wherein said racemate is treated with dehydroabietylamine at a temperature of from 40° to the reflux temperature of said solvent and crystallization is effected by cooling to a temperature of from 0° to 35°C.

8. A process for preparing the L-antipode of a salt of the formula

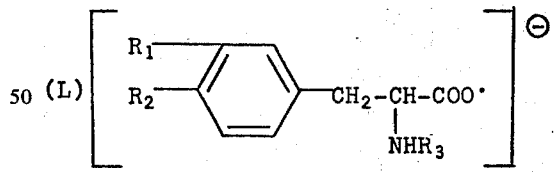

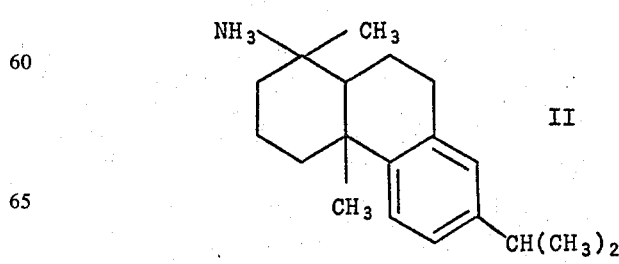

wherein $R_1$ is methoxy; $R_2$ is hydroxy; and $R_3$ is benzoyl
comprising treating a solution containing a racemate of the formula

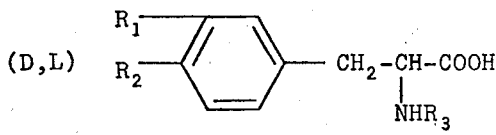   I wherein $R_1$, $R_2$ and $R_3$ are as above
in an inert organic solvent with from 0.4 to 0.6 moles of a base selected from the group consisting of alkali metal hydroxides, organic amines and ammonia and with from 0.4 to 0.6 moles of dehydroabietylamine to form said L-antipode of said salt as a precipitate.

9. The process of claim 8 wherein said solvent is a lower alkanol.

10. The process of claim 8 wherein said racemate is treated with dehydroabietylamine at a temperature of from 40° to the reflux temperature of said solvent and crystallization is effected by cooling to a temperature of from 0° to 35°C.

11. A process for resolving into its L-enantiomorph, a racemate of the formula

I wherein $R_1$ is methoxy; $R_2$ is hydroxy; and $R_3$ is benzoyl
which comprises treating a solution of said racemate in an organic solvent with dehydroabietylamine to obtain as a crystalline precipitate a salt of the formula

II wherein $R_1$, $R_2$ and $R_3$ are as above;
separating said salt from the solution; and then neutralizing said salt with an acid or base to form the L-enantiomorph of said racemate.

12. The process of claim 11 wherein said solvent is a lower alkanol.

13. The process of claim 11 wherein said racemate is treated with dehydroabietylamine at a temperature of from 40° to the reflux temperature of said solvent and crystallization is effected by cooling to a temperature of from 0° to 35°C.

14. A process for resolving into its L-enantiomorph a racemate of the formula:

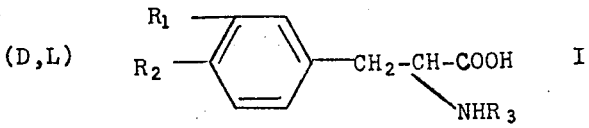   I wherein $R_1$ is methoxy; $R_2$ is hydroxy; and $R_3$ is benzoyl;
which comprises treating a solution of said racemate in an organic solvent with a base selected from the group consisting of alkali metal hydroxides, organic amines and ammonia in a molar ratio of from 0.4 to 0.6 moles of said base per mole of said racemate and dehydroabietylamine in a molar ratio of from 0.4 to 0.6 moles of said dehydroabietylamine per mole of said racemate to obtain as a crystalline precipitate a salt of the formula:

wherein $R_1$, $R_2$ and $R_3$ are as above;
separating said salt from the solution; and then neutralizing said salt with an acid or base to form the L-enantiomorph of said racemate.

15. The process of claim 14 wherein said solvent is a lower alkanol.

16. The process of claim 14 wherein said racemate is treated with dehydroabietylamine at a temperature of from 40° to the reflux temperature of said solvent and crystallization is effected by cooling to a temperature of from 0° to 35°C.

17. The compound D-N-benzoyl-3-(4-hydroxy-3-methoxyphenyl)-alanine.

18. The compound L-N-benzoyl-3-(4-hydroxy-3-methoxyphenyl)-alanine.

19. In a process for preparing L-Dopa from DL-α-benzoylamino-4-hydroxy-3-methoxydihydrocinnamic acid the step which comprises contacting said acid with dehydroabietylamine to form the dehydroabietylamine salt of L-α-benzoylamino-4-hydroxy-3-methoxydihydrocinnamic acid followed by neutralization with hydrochloric acid and hydrolysis with 48 percent hydrobromic acid.

* * * * *